US010066256B2

(12) United States Patent
Jouvenot et al.

(10) Patent No.: US 10,066,256 B2
(45) Date of Patent: Sep. 4, 2018

(54) DETECTION OF GENOME EDITING

(71) Applicant: Bio-Rad Laboratories, Inc., Hercules, CA (US)

(72) Inventors: Yann Jouvenot, Benicia, CA (US); Nick Heredia, Mountain House, CA (US); Viresh Patel, San Ramon, CA (US); Samantha Cooper, Berkeley, CA (US); Jen Berman, San Carlos, CA (US); Eli Hefner, Fairfield, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 204 days.

(21) Appl. No.: 15/073,388

(22) Filed: Mar. 17, 2016

(65) Prior Publication Data

US 2016/0273023 A1     Sep. 22, 2016

Related U.S. Application Data

(60) Provisional application No. 62/134,517, filed on Mar. 17, 2015.

(51) Int. Cl.
  *C12Q 1/68*  (2018.01)
  *C12Q 1/6806*  (2018.01)
  *C12Q 1/6809*  (2018.01)
  *C12Q 1/6827*  (2018.01)

(52) U.S. Cl.
  CPC ......... *C12Q 1/6806* (2013.01); *C12Q 1/6809* (2013.01); *C12Q 1/6827* (2013.01)

(58) Field of Classification Search
  None
  See application file for complete search history.

(56) References Cited

U.S. PATENT DOCUMENTS

| | | |
|---|---|---|
| 2011/0143949 A1 | 6/2011 | Heid et al. |
| 2013/0316358 A1 | 11/2013 | Navon et al. |
| 2013/0326645 A1 | 12/2013 | Cost et al. |
| 2014/0315985 A1 | 10/2014 | May et al. |

FOREIGN PATENT DOCUMENTS

WO     2014/189628 A1     11/2014

OTHER PUBLICATIONS

Sutherland et al. Evaluation of number average length analysis in quantifying double strand breaks in genomic DNA. Biochemistry (2003) 42:3375-3384. (Year: 2003).*
Filippova et al. Quantifying double-strand breaks and clustered damages in DNA by single-molecule laser fluorescence sizing. Biophysical Journal (2003) 84:1281-1290. (Year: 2003).*
Yan et al. BLISS is a versatile and quantitative method for genome-wide profiling of DNA double-strand breaks. Nature Communications (2017) DOA: 10.1038/ncomms 15058, pp. 1-9. (Year: 2017).*
International Search Report and Written Opinion from PCT/US2016/022962, dated Jun. 20, 2016.
Pfeiffer, et al., "Mechanisms of DNA Double-Strand Break Repair and their Potential to Induce Chromosomal Aberrations", Mutagenesis, vol. 15, No. 4, Jul. 2000, pp. 289-302.
Tsai, et al., "GUIDE—Seq enables genome-wide profiling of off-target cleavage by CRISPR—Cas nucleases", HHS Public Access—Nat Biotechnol, Author manuscript, Aug. 2015, pp. 1-23.
Extended European Search Report for EP Application 16765783.2 dated Jun. 29, 2018; 12 pages.
Chailleux, C. et al.; "Quantifying DNA double-strand breaks induced by site-specific endonucleases in living cells by ligation-mediated purification". *Nature Protocols*; vol. 9, No. 3, Feb. 6, 2014; pp. 517-528.
Filippova, E.M. et al.; "Quantifying Double-Strand Breaks and Clustered Damages in DNA by Single-Molecule Laser Fluorescence Sizing"; *Biophysical Journal*; vol. 84, No. 2; Feb. 1, 2003; pp. 1281-1290.
Friedl. A.A. et al.; "An electrophoretic approach to the assessment of the spatial distribution of DNA double-strand breaks in mammalian cells"; *Electrophoresis*; vol. 16; Oct. 1, 1995; pp. 1865-1874.
Ochman, H. et al.; "Genetic Applications of an Inverse Polymerase Chain Reaction"; *Genetics*; vol. 120, No. 3; Nov. 1, 1988; Genetics Society of America, Austin, TX; pp. 621-623.
Pavlopoulos, A. ed; Bugert et al.; Identification of DNA Sequences that Flank a Known Region by Inverse PCR; Chapter 16; *Molecular Typing of Blood Cell Antigens in: Methods in Molecular Biology*; vol. 772; Jan. 1, 2011; Humana Press, US; pp. 267-275.
Pinto, M. et al.; "Quantification of radiation induced DNA double-strand breaks in human fibroblasts by PFGE: testing the applicability of random breakage models"; *International Journal of Radiation Biology*; vol. 78, No. 5; Jan. 1, 2002; pp. 375-388.
Shee, C. et al.; "Engineered proteins detect spontaneous DNA breakage in human and bacterial cells"; *ELIFE*; Oct. 29, 2013; pp. 1-25.
Sutherland, B.M. et al.; "Evaluation of Number Average Length Analysis in Quantifying Double Strand Breaks in Genomic DNAs +"; *Biochemistry*; vol. 42, No. 11; Mar. 1, 2003; pp. 3375-3384.

* cited by examiner

*Primary Examiner* — David C Thomas
(74) *Attorney, Agent, or Firm* — Kilpatrick Townsend and Stockton LLP

(57) ABSTRACT

Methods, compositions, and kits are provided for quantifying a number or frequency of double stranded breaks in the genome of a cell or in the genomes of a population of cells.

21 Claims, 6 Drawing Sheets

DETECTION OF GENOME EDITING

CROSS-REFERENCES TO RELATED APPLICATIONS

This application claims priority to U.S. Provisional Patent application 62/134,517, filed on Mar. 17, 2015, the contents of which are hereby incorporated in the entirety for all purposes.

BACKGROUND OF THE INVENTION

Double strand break points can occur in the genome of a cell through a variety of different mechanisms. For example, chemical mutagens, high intensity magnetic fields, or ionizing radiation can introduce double strand break points. As another example, double strand break points can be introduced into a genome by various genome editing reagents or methods.

An ideal genome editing reagent would only create a double strand break point at one or more "on-target" sites in the genome. However, current genome editing reagents often generate double-stranded break points at one or more "off-target" sites in the genome. In some cases, such off-target sites are highly homologous to an on-target site. For a genome of known sequence and having a small number of highly homologous off-target sites, such highly homologous off-target sites can be identified and assayed for editing using any number of available methods. However, the position, number, and frequency of off-target editing is generally not predictable. In addition, double-stranded breaks introduced by chemical mutagens, high intensity magnetic fields, or ionizing radiation are by their nature unpredictable.

Definitive identification and quantitation of double-stranded breaks throughout the genome of a cell can be performed by whole genome next generation sequencing. However, this can be quite costly and time-consuming, and can be impractical for assaying a population of cells (e.g., a population of cells obtained from a sample of an organism), or for optimizing genome editing reagents and methods.

BRIEF SUMMARY OF THE INVENTION

In a first aspect, the present invention provides a method for quantitating a number of double stranded break points in a genome of a cell, the method comprising: a) providing genomic nucleic acid from the cell, wherein the genomic nucleic acid has an exogenous donor polynucleotide, or a portion thereof, inserted into double stranded break points in the cell; b) fragmenting the genomic nucleic acid to generate a plurality of genomic nucleic acid fragments, wherein at least one of the genomic nucleic acid fragments contains the inserted donor polynucleotide or the portion thereof; c) generating a plurality of mixture partitions containing circular genomic nucleic fragments and a pair of amplification primers, wherein the pair of amplification primers are complementary to opposite strands of the donor polynucleotide or portion thereof, and wherein the pair of amplification primers are oriented such that the 5' ends are proximal to each other and the 3' ends are distal to each other when hybridized to a genomic nucleic fragment containing the inserted donor polynucleotide or portion thereof before circularization; d) amplifying the genomic nucleic fragments with the pair of amplification primers to selectively generate amplicons in mixture partitions that contain one or more genomic fragments containing the inserted donor polynucleotide or portion thereof; e) detecting the amplicons; and f) counting the number of mixture partitions containing amplicons, thereby quantitating a number of double stranded break points in the genome of the cell.

In a second aspect, the present invention provides, a method for detecting or quantifying a number of double stranded break points in a genome of a cell comprising: providing genomic nucleic acid fragments, wherein at least a portion of the genomic nucleic acid fragments comprise an inserted exogenous donor oligonucleotide; partitioning the fragments; incubating the partitions under conditions suitable to selectively amplify partitions containing fragments that comprise an insertion; detecting selective amplification products in the partitions; and quantifying the number of partitions in which a selective amplification product is detected.

In some embodiments, generating the plurality of mixture partitions containing circular genomic nucleic fragments comprises circularizing the genomic nucleic acid fragments and partitioning the circularized genomic nucleic fragments into a plurality of mixture partitions. In some embodiments, the generating the plurality of mixture partitions containing circular genomic nucleic fragments comprises partitioning the genomic nucleic fragments into a plurality of mixture partitions and circularizing the genomic fragments in the partitions. In some embodiments, the method further comprises performing a)-f) for a population of cells, thereby quantitating a number of double-stranded break points in the genomes of the population of cells. In some embodiments, at least one of the double stranded break points is induced by an exogenous genome editing reagent. In some embodiments, at least one of the double stranded break points is induced by a chemical mutagen or ionizing radiation.

In some embodiments, the donor polynucleotide is a double stranded donor polynucleotide. In some cases, the double stranded donor polynucleotide comprises a 5' or 3' phosphorothioate linkage. In some cases, the double stranded donor polynucleotide comprises 5' and 3' phosphorothioate linkages. In some cases, the double stranded donor polynucleotide comprises blunt 5' and 3' ends. In some cases, the double stranded donor polynucleotide is 5' phosphorylated. In some cases, the double stranded donor polynucleotide is from 20 to 150 bp in length. In some cases, the double stranded donor polynucleotide is from 25 to 50 bp in length. In some cases, the double stranded donor polynucleotide is from 30 to 40 bp in length. In some cases, the double stranded donor polynucleotide is 34 bp in length.

In some embodiments, the donor polynucleotide is single stranded. In some embodiments, the 5' ends of the pair of amplification primers hybridize to an overlap region on opposite strands of the donor polynucleotide. In some embodiments, the overlap region is 1, 2, 3, 4, 5, 6, 7, 8, 9, or 10 nucleotides in length. In some embodiments, the method comprises linearizing circular genomic nucleic fragments that contain the inserted donor polynucleotide or portion thereof in the partitions and amplifying the linearized circular genomic nucleic acid fragments. In some cases, the linearizing comprises cleaving the inserted donor polynucleotide or portion thereof.

In some embodiments, the fragmenting comprises random shearing of the genomic DNA. In some embodiments, the fragmenting comprises contacting the genomic DNA with a nuclease. In some cases, the contacting the genomic DNA with a nuclease is performed under conditions suitable to generate an average fragment length of about 256 bp. In some cases, the nuclease cleaves (e.g., recognizes and cleaves) a four base pair recognition site. In some cases, the circularizing comprises ligation.

In some embodiments, the detecting the amplicons comprises detecting an increase in fluorescence of an intercalating dye in the presence of a double stranded DNA amplicon. In some cases, the increase in fluorescence of the intercalating dye in the mixture partitions is quantified to thereby detect a size of the amplicons in the mixture partitions. In some embodiments, the method further comprises detecting an endogenous nucleic acid sequence of the genome by amplifying the endogenous nucleic acid sequence in the presence of an endogenous reference probe that specifically detects the endogenous genomic sequence.

In some embodiments, the method further comprises detecting a heterologous sequence that is heterologous to the genome of the organism and is generated by ligation of two endogenous non-consecutive genomic nucleic acid fragments, wherein the detecting the heterologous sequence comprises amplifying the heterologous sequence in the presence of a heterologous reference probe that specifically detects the heterologous sequence. In some embodiments, the method further comprises detecting a heterologous sequence that is heterologous to the genome of the organism and is generated by circularization (e.g., ligation) of a genomic nucleic acid fragment, wherein the detecting the heterologous sequence comprises amplifying the heterologous sequence in the presence of a heterologous reference probe that specifically detects the heterologous sequence. In some cases, the reference probe is a hydrolysis probe or a molecular beacon.

In some cases, the reference probe detects a sequence proximal to an on-target genome-editing reagent cleavage site. In some cases, the method comprises counting the number of mixture partitions that contain an amplicon and a sequence proximal to an on-target genome-editing reagent cleavage site, thereby detecting a number of on-target genome insertions. In some cases, the method comprises comparing the ratio of i) to ii), wherein: i) is a number of mixture partitions containing an amplicon and a sequence proximal to an on-target genome-editing reagent cleavage site; and ii) is a number of mixture partitions containing an amplicon, thereby determining a rate of on-target genome editing by a genome editing reagent or method.

In some cases, the method comprises counting the number of mixture partitions that contain an amplicon and do not contain a sequence proximal to an on-target genome-editing reagent cleavage site, thereby detecting a number of off-target genome insertions. In some cases, the method comprises comparing a ratio of i) to ii), wherein: i) is a number of mixture partitions that contain an amplicon and do not contain a sequence proximal to an on-target genome-editing reagent cleavage site; and ii) is a number of mixture partitions containing an amplicon, thereby determining a rate of off-target genome insertions by a genome editing reagent or method.

In some embodiments, the plurality of mixture partitions comprise emulsion droplets. In some embodiments, the plurality of mixture partitions comprise micro-, nano-, or pico-liter wells or reaction chambers.

DEFINITIONS

Figure 1:
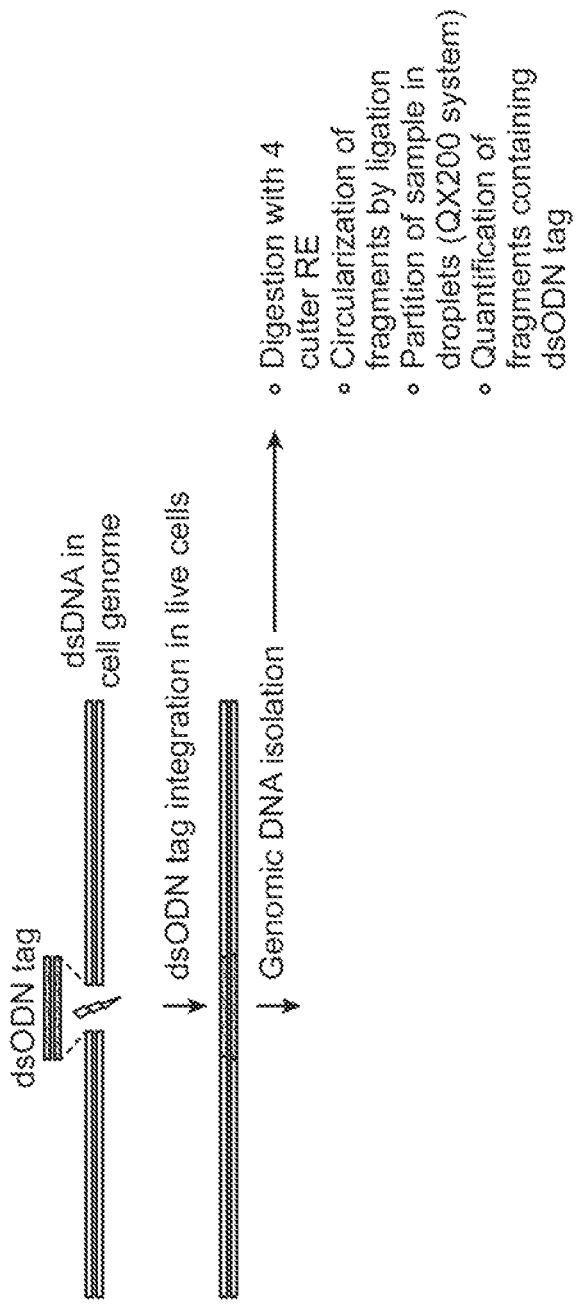
FIG. 1: depicts a flow chart describing a method for quantitating double stranded break points in a cell. In this embodiment, a double stranded donor oligonucleotide (dsODN) is inserted into double stranded break points in the genome of a cell. Genomic DNA is isolated, digested with a restriction enzyme that recognizes a four base pair cleavage site, circularized by ligation, partitioned into droplets, and quantified by selective amplification of fragments containing a dsODN, or portion thereof.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Spring Harbor Lab Press (Cold Spring Harbor, N.Y. 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein, the terms "double strand break," "double strand break point," and the like refer to cleavage sites of double stranded genomic DNA in a cell, in which a pair of proximal phosphodiester bonds on opposite strands of the double stranded genomic DNA is hydrolyzed. Such double stranded breaks can be produced, e.g., by a restriction endonuclease, a Cas9 nuclease, a nickase (e.g., a TALEN, Zinc-Finger, or CRISPR/Cas based nickase), a chemical mutagen, ionizing radiation, or a high intensity magnetic field. Typically, the pair of hydrolyzed proximal phosphodiester bonds on opposite strands of the double stranded genomic DNA are within about 1,000; 900, 800, 700, 600, 550, 500, 450, 400, 350, 300, 250, 200, 150, 100, 75, 50, 25, 18, 15, 14, 13, 12, 11, 10, 9, 8, 7, 6, 5, 4, 3, 2, or 1 nucleotides of each other.

As used herein, the term "genome editing reagent" refers to a reagent (e.g., typically a reagent that contains a nuclease or nickase) that is capable of specifically cleaving or nicking a genomic sequence to create a double stranded break. Exemplary genome editing reagents that can introduce double strand break points include, but are not limited to, CRISPR/Cas9 reagents, TALENS, zinc-finger nucleases, engineered meganucleases, and combinations thereof. In some cases, the genome editing reagent contains or includes a pair of targeted nickase enzymes that is capable of specifically introducing proximal nick sites into a genomic sequence. The genome editing reagent can be configured to introduce a cleavage or nick pair site into which an exogenous donor oligonucleotide can be inserted.

As used herein an "on-target" genome editing reagent cleavage site refers to genome editing reagent cleavage site having perfect homology to a cleavage site to which a genome editing reagent is targeted. Similarly, an "off-target" genome editing reagent cleavage site refers to a cleavage site that differs from the target site by 1, 2, 3, 4, 5, 6, 7, 8, 9, 10, 11, 12, 13, 14, 15, 16, 17, 18, 19, 20, or more substitutions, deletions, or insertions.

As used herein, the term "linearized" refers a genomic nucleic acid fragment that has been circularized by joining (e.g., ligating) the two free ends of the fragment, and then linearized by cleaving the circularized genomic nucleic acid fragment. The circularized genomic acid fragment can be linearized by cleaving an inserted donor oligonucleotide in the circularized fragment. Conversely, the term "linear" refers to a genomic nucleic acid fragment that has not been circularized.

As used herein, the term "partitioning" or "partitioned" refers to separating a sample into a plurality of portions, or "mixture partitions." Mixture partitions can be solid or fluid. In some embodiments, a mixture partition is a solid partition, e.g., a micro channel, micro well, or microcapsule. In some embodiments, a mixture partition is a fluid partition, e.g., a droplet. In some embodiments, a fluid partition (e.g., a droplet) is a mixture of immiscible fluids (e.g., water and oil), or an emulsion. In some embodiments, a fluid partition (e.g., a droplet) is an aqueous droplet that is surrounded by an immiscible carrier fluid (e.g., oil). In other embodiments, a fluid partition is an aqueous droplet that is physically or chemically separated from adjacent aqueous droplets such that the contents of one droplet does not diffuse into adjacent droplets.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 (e.g., 10-50, 12-35, 15-35, 12-30, 15-30, 12-25, 15-25, 12-18, or 15-18) contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is 37, 40, 42, 45, 50, 55, 60, 65, 70, 75, or 80° C. In some embodiments, the defined temperature at which specific hybridization occurs is from 45-75° C., from 45-70° C., from 45-65° C., from 45-60° C., from 45-55° C., from 50-75° C., from 50-70° C., from 50-65° C., from 50-60° C., or from 50-55° C.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

The term "probe" refers to a molecule (e.g., a protein, nucleic acid, aptamer, etc.) that specifically interacts with or specifically binds to a target molecule. Non-limiting examples of molecules that specifically interact with or specifically bind to a target molecule include nucleic acids (e.g., oligonucleotides), proteins (e.g., antibodies, transcription factors, zinc finger proteins, non-antibody protein scaffolds, etc.), and aptamers. A probe can be conjugated (e.g., covalently conjugated to a detectable label.

The term "genomic nucleic acid," "genomic DNA," and the like refers to bacterial or eukaryotic DNA. The genomic DNA can be DNA from one or more, or all, of the chromosomes of a cell. The genomic DNA can further, or alternatively, include DNA from one or more, or all, organelles of a cell.

The terms "label" and "detectable label" interchangeably refer to a composition detectable by spectroscopic, photochemical, biochemical, immunochemical, chemical, or other physical means. For example, useful labels include fluorescent dyes, luminescent agents, radioisotopes (e.g., $^{32}$P, $^3$H), electron-dense reagents, enzymes, biotin, digoxigenin, or haptens and proteins, nucleic acids, or other entities which can be made detectable, e.g., by incorporating a radiolabel into a probe (e.g., oligonucleotide, peptide, or antibody) specifically reactive with a target molecule. Any method known in the art for conjugating an antibody to the label can be employed, e.g., using methods described in Hermanson, *Bioconjugate Techniques* 1996, Academic Press, Inc., San Diego.

A molecule that is "linked" to a label (e.g., as for a labeled probe as described herein) is one that is bound, either covalently, through a linker or a chemical bond, or noncovalently, through ionic, van der Waals, electrostatic, or hydrogen bonds to a label such that the presence of the molecule can be detected by detecting the presence of the label bound to the molecule.

The term "exogenous" in the context of an exogenous donor oligonucleotide refers to a donor oligonucleotide that is not naturally occurring in the genome of the cell. The exogenous donor oligonucleotide can be inserted into double-stranded break points in the genome of a cell by, e.g., one or more components or activities of a non-homologous end joining or homology directed repair pathway of a cell.

DETAILED DESCRIPTION OF THE INVENTION

Described herein are methods and compositions for assaying double stranded breaks in a genome of a cell, or in the genomes of a population of cells (see, e.g., FIG. 1). Methods and compositions described herein can be used for assessing the toxicity of an exogenous insult (e.g., exposure to a chemical mutagen, intense magnetic field, or ionizing radiation). Methods and compositions described herein can also be used for assessing or optimizing the fidelity of a genome editing reagent or method. For example, genome editing can be performed on a cell or population of cells, and methods or compositions described herein can be used to detect and/or quantitate either on-target or off-target genome editing, or a combination thereof. Methods and compositions described herein can also be used to quantitate or monitor a number or frequency of genome edited cells in a host organism.

The methods involve providing genomic DNA comprising inserted donor polynucleotides and generating conditions in which DNA fragments comprising insertions are selectively amplified (e.g., by inverse PCR) and quantified by partitioning.

I. Methods

Described herein are methods for quantitating double stranded break points in a genome of cell. Such quantitation can include one or more of the following steps: a) providing genomic nucleic acid from the cell, wherein the genomic nucleic acid has an exogenous donor polynucleotide, or a portion thereof, inserted into double stranded break points in the cell; b) fragmenting the genomic nucleic acid to generate a plurality of genomic nucleic acid fragments, wherein at least one of the genomic nucleic acid fragments contains the inserted donor polynucleotide or the portion thereof; c) generating a plurality of mixture partitions containing circular or linearized genomic nucleic fragments and an amplification primer or pair of amplification primers adapted to selectively amplify target template in partitions containing genomic nucleic acid fragments having an inserted donor polynucleotide, or portion thereof; d) amplifying the genomic nucleic fragments with the amplification primer or pair of amplification primers under conditions to selectively generate amplicons in mixture partitions that contain one or more genomic fragments containing the inserted donor polynucleotide or portion thereof; e) detecting the amplicons; and f) counting the number of mixture partitions containing amplicons, thereby quantitating a number of double stranded break points in the genome of the cell.

a) Providing Genomic Nucleic Acid from a Cell or Population of Cells

Genomic nucleic acid can be provided from a variety of cells. For example, a cell or population of cells can be subject to an exogenous insult such as a chemical mutagen, intense magnetic field, or ionizing radiation. As another example, a cell or population of cells can be contacted with a genome editing reagent. Exemplary genome editing reagents include, but are not limited to, CRISPR/Cas9 reagents (e.g., CRISPR/Cas9 nucleases, nickases, or nickase pairs), TALENS (e.g., TALEN nucleases, nickases, or nickase pairs), zinc-finger nucleases (e.g., Zinc-finger nucleases, nickases, or nickase pairs), engineered meganucleases (e.g., meganucleases, nickases, or nickase pairs), and combinations thereof. Exemplary CRISPR/Cas9 reagents include, but are not limited to, those described in U.S. Appl. Pub. Nos: 2014/0248702; 2014/0315985; 2013/0130248; and 2014/0068797; U.S. Pat. No. 8,697,359; and Ran et al., Nature. 2015 Apr. 9; 520(7546):186-91, Zetsche et al., Cell. 2015 Oct. 22; 163(3):759-71, and Slaymaker et al., Science. 2016 Jan. 1; 351(6268):84-8. Exemplary TALEN reagents include, but are not limited to, those described in Miller et al., Nat Biotechnol. 2011 February; 29(2):143-8.

The exogenous insult or genome editing reagent can introduce one or more double stranded break points in the one or more cells. An exogenous donor polynucleotide can simultaneously or subsequently be contacted with the one or more cells. The contacting can be performed under conditions suitable to insert the donor polynucleotide into one or more of the double stranded break points. Genomic nucleic acid can then be obtained from the one or more cells and provided for use in a double stranded break point assay as described herein.

The cell or population of cells can be subject to the exogenous insult or contacted with the genome editing reagent in vitro or in vivo. For example, primary cells or a cell line can be subject to the exogenous insult or contacted with the genome editing reagent in vitro. Primary cells can be extracted from a host and subject to the exogenous insult or contacted with the genome editing reagent and then assayed for double stranded break points according to one or more methods described herein. An exogenous donor polynucleotide can simultaneously or subsequently be contacted with the one or more cells. In some cases, an exogenous donor polynucleotide can be contacted with the one or more cells prior to contact with the genome editing reagent such that sufficient donor polynucleotide is present during cleavage by the editing reagent. The contacting of the one or more cells with the donor polynucleotide can be performed under conditions suitable to insert the donor polynucleotide into one or more of the double stranded break points.

As another example, a host organism can be subject to an exogenous insult (e.g., exposure to a chemical mutagen, intense magnetic field, or ionizing radiation) or contacted with a genome editing reagent, and cells can then be extracted and analyzed to determine a quantity or frequency of double-stranded break points. In some cases, primary cells are extracted from a host after the host is subject to the exogenous insult or contacted with the genome editing reagent under conditions suitable to insert a donor polynucleotide into one or more of double stranded break points, and then a portion of the cells can be assayed for double stranded break points according to one or more methods described herein. In some cases, the remainder of the extracted cells are used for additional or alternative applications. For example, the remainder of the extracted cells can be assayed for proliferation, proliferative potential, viability, cytotoxic activity, etc. In some cases, cells are extracted from a host, prior to or after being subject to genome editing, a portion of the genome edited cells are assayed for on-target and/or off-target editing, and a portion of the genome edited cells are introduced back into the same or a different host.

In some cases, edited cells containing a donor polynucleotide (e.g., cells from a host or heterologous cells) are introduced into a host, and one or more samples are subsequently obtained from the host. Cells from the one or more samples can be assayed using a method described herein to monitor or assay the number or frequency of edited cells in the host.

Genomic DNA can be purified from cells as desired.

b) Fragmenting Genomic Nucleic Acid

Figure 4:
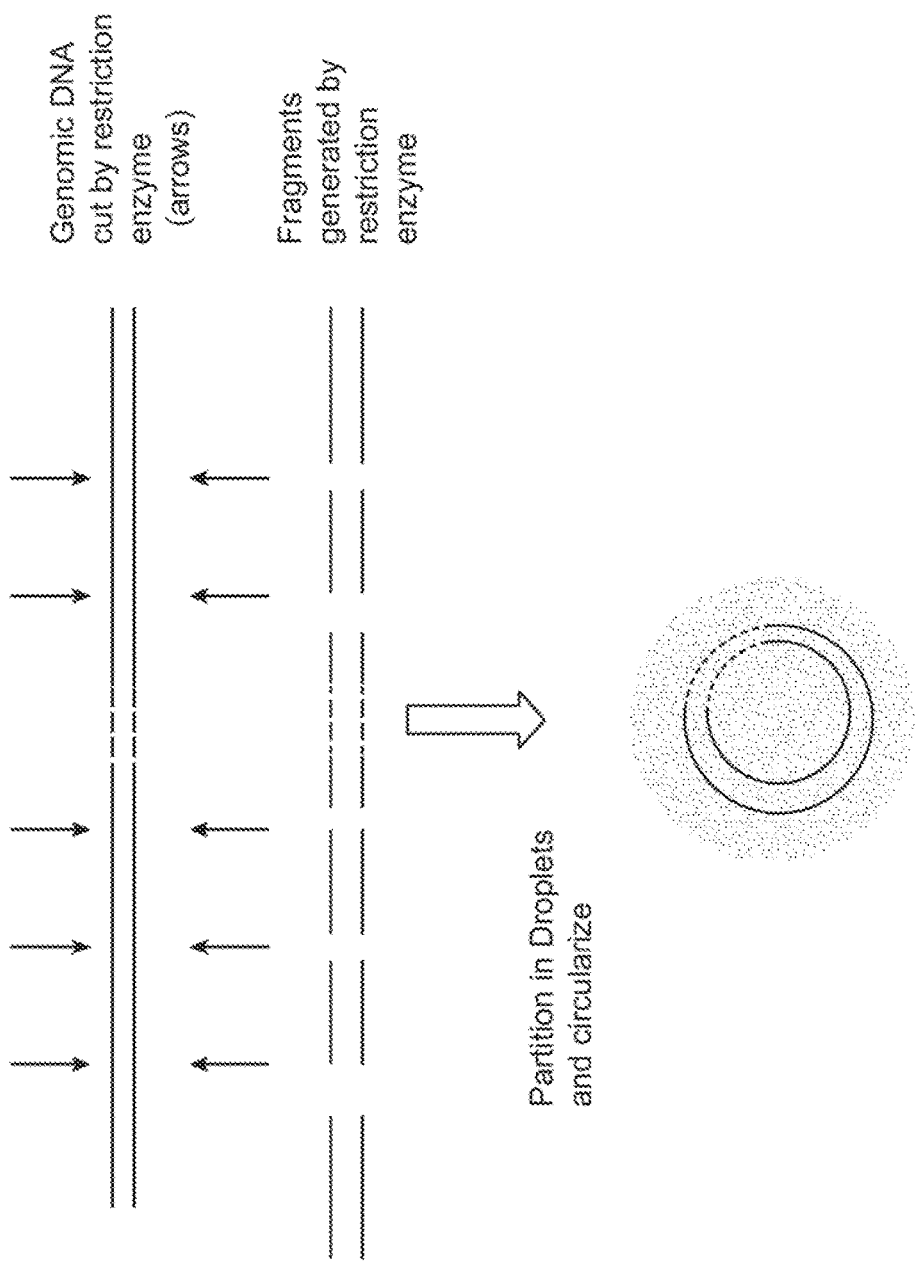
FIG. 4: depicts an embodiment of a portion of a quantitative assay for double stranded break points in a genome of a cell. In this embodiment, genomic DNA is fragmented, partitioned in droplets, then circularized. Solid lines indicate genomic DNA. Dotted lines indicate inserted exogenous donor oligonucleotide.

Genomic nucleic acid can be fragmented by a variety of methods known in the art. For example, genomic nucleic acid can be fragmented by physical, chemical, or enzymatic means. Physical shearing can include sonication, nebulization (e.g., as described in WO/1992/007091), forcing a liquid medium containing the nucleic acid through an orifice at high pressure (e.g., using a French press), hydrodynamic shearing, or high performance liquid chromatography. Enzymatic fragmentation can be performed with a nuclease. In some cases, the fragmentation is performed with a non-specific nuclease such as DNase I, or micrococcal nuclease. In some cases, the fragmentation is performed with one or more restriction endonucleases (see, e.g., FIG. 4). Exemplary nucleases, or nuclease mixtures, further include, but are not limited to, those containing T7-Endo I, non-specific nuclease *Vibrio vulnificus*, fragmentase (NEB), a transposase, or a combination thereof. The fragmented genomic nucleic acid can be single or double stranded, or a combination thereof.

In one embodiment, the genomic nucleic acid is amplified in the presence of dUTP and the resulting amplified genomic nucleic acid containing uracil is contacted with uracil DNA glycosylase to obtain fragments. In some cases, the genomic nucleic acid is fragmented before amplification in the presence of dUTP. For example, the genomic nucleic acid can be fragmented under conditions suitable to generate large fragments (e.g., fragments having an average size of at least about 1,000; 2,000; 5,000; 10,000; 30,000 base pairs in length or larger). The large fragments can be optionally purified, and amplified in the presence of dUTP to incorporate uracils. The amplicons can then be contacted with uracil DNA glycosylase to obtain smaller fragments.

In some embodiments, the fragmentation results in single or double stranded ends for which the sequence adjacent to the end is random or unknown. The sequence adjacent to the end may be, or may be at least, 2 bases, 3 bases, 4 bases, 5 bases, 6 bases, 8 bases, 10 bases, 20 bases, 30 bases, or 50 bases. Such random or unknown fragment ends can be obtained by, for example, physically shearing the genomic nucleic acid, contacting the nucleic acid with a non-specific nuclease, or fragmenting uracil incorporated genomic nucleic acid amplicons.

In some embodiments, the fragmentation results in single or double stranded ends for which the sequence adjacent to the end is known or non-random. The sequence adjacent to the end may be, or may be at least, 2 bases, 3 bases, 4 bases, 5 bases, 6 bases, 8 bases, 10 bases, 20 bases, 30 bases, or 50 bases. Such non-random or known fragment ends can be obtained by, for example, contacting the nucleic acid with one or more restriction endonucleases. In one embodiment, the genomic nucleic acid is fragmented by a method that does not fragment at or within a region of inserted exogenous donor polynucleotide. For example, the genomic nucleic acid can be fragmented with one or more restriction endonucleases that do not cleave within the exogenous donor polynucleotide sequence.

The fragmenting can be performed under conditions suitable to generate a fragment size or fragment size range. The fragment size or fragment size range can be an average (e.g., mean or median) fragment size or fragment size range. For example, the fragment size can be, or be about, 50, 75, 100, 125, 150, 175, 200, 225, 250, 256, 275, 300, 325, 300, 325, 350, 375, 400, 450, 425, 450, 475, 500, 525, 550, 575, 600, 650, 700, 750, 800, 850, 900, 950, or 1000 bases or base pairs, or more. As another example, the fragment size range can be from, or from about, 50, 75, 100, 125, 150, 175, 200, 225, 250, 256, 275, 300, 325, 350, 400, 425, 450, 475, or 500 bases or base pairs to about 75, 100, 125, 150, 175, 200, 225, 250, 256, 275, 300, 325, 350, 400, 425, 450, 475, 500; 525, 550, 575, 600, 650, 700, 750, 800, 850, 900, 950, or 1000 bases or base pairs, or more.

In some embodiments, the genomic nucleic acid is fragmented by one or more restriction endonucleases selected to provide one or more of the foregoing fragment sizes or size ranges. In some cases, the genomic nucleic acid is fragmented with a restriction endonuclease that recognizes and cleaves a four base pair site. Such "four cutters" are expected to produce a fragment size average of about $4^4$, equal to 256 base pairs, assuming a random distribution nucleotides in the genome. In some cases, the genomic nucleic acid is fragmented by one or more restriction endonucleases to provide one or more of the foregoing fragment sizes or size ranges, and complementary or partially complementary single stranded overhanging ends. Such "sticky ends" can facilitate circularization of fragments (e.g., intramolecular circularization under limiting dilution or in partitions).

In some cases, the fragmenting is performed under conditions suitable to generate one or more of the foregoing fragment sizes or fragment size ranges. For example, temperature, time, degree or intensity of physical shearing, endonuclease concentration, or amount of uracil incorporation (e.g., controlled by concentration of uracil in the incorporation reaction) can be altered to obtain a desired fragment size or fragment size range. Genomic nucleic acid that is fragmented by one or more enzymes can be treated to inactivate the fragmenting enzyme. For example, if a fragmenting enzyme is metal dependent, the genomic nucleic acid can be contacted with a chelating agent. As another example, a fragmenting enzyme can be heat-inactivated. In some cases, the genomic nucleic acid is contacted with one or more of the foregoing specific or non-specific fragmenting enzymes and then the fragmenting enzyme is inactivated when a selected fragment size or size range is achieved.

In some cases, genomic nucleic acid is fragmented and then a selected fragment size or fragment size range is extracted or purified. Methods for extracting or purifying a selected fragment size or size range include HPLC, size exclusion chromatography, gel electrophoresis, solid phase reversible immobilization (e.g., using AMPURE® XP beads), capillary electrophoresis, and the like. The selected fragment size or fragment size range can be extracted or purified prior to, subsequent to, of in conjunction with one or more other fragmenting enzyme inactivation methods or one or more nucleic acid purification methods.

Fragmented genomic nucleic acid can be purified. Methods and compositions for purifying fragmented genomic nucleic acid include but are not limited to phenol, chloroform, or phenol:chloroform:isoamyl alcohol extraction; ethanol or isopropanol precipitation; anionic exchange chromatography; silica gel chromatography; solid phase reversible immobilization; HPLC, size exclusion chromatography, gel electrophoresis, capillary electrophoresis, or a combination thereof. Fragmented genomic nucleic acid can be purified prior to, subsequent to, of in conjunction with one or more other fragmenting enzyme inactivation methods or one or more fragment size or fragment size range extraction methods.

c) Generating a Plurality of Mixture Partitions

Fragmented genomic nucleic acid can be partitioned into a plurality of mixture partitions. Methods and compositions for partitioning a sample (e.g., a sample of fragmented genomic nucleic acid) are described, for example, in published patent applications WO 2010/036,352, US 2010/0173,394, US 2011/0092,373, and US 2011/0092,376, the contents of each of which are incorporated herein by reference in the entirety. The plurality of mixture partitions can be in a plurality of emulsion droplets, or a plurality of microwells, etc.

The fragmented genomic nucleic acid can be partitioned prior to circularizing, or after circularizing. For example, genomic nucleic acid fragments can be circularized, and then partitioned into a plurality of mixture partitions. As another example, genomic nucleic acid fragments can be partitioned into a plurality of mixture partitions and circularized therein. The circularizing of genomic fragments can be performed by ligation using a DNA ligase enzyme. In some embodiments, the circularizing is performed under dilute conditions prior to partitioning, such that intramolecular circularization is favored over intermolecular circularization. In some embodiments, the circularization is performed under conditions such that at least, or at least about, 10%, 20%, 25%, 30%, 35%, 40%, 45%, 50%, 55%, 60%, 65%, 70%, 75%, 80%, 85%, 90%, 95%, 97.5%, 98%, 99%, 99.5%, 99.75%, 99.9%, or more of the circularization is intramolecular. In some embodiments, all, or substantially all, of the circularization is intramolecular.

In some embodiments, genomic nucleic acid fragments are circularized to generate circular genomic nucleic acid fragments, and then the portion of the genomic nucleic acid fragments that contain an inserted exogenous donor polynucleotide is linearized by cleaving such circularized genomic nucleic acid fragments at a sequence contained within the donor polynucleotide. In some cases, the circularization and linearization is performed prior to partitioning. In some cases, the circularization is performed prior to partitioning, the circular fragments are partitioned, and then the linearization is performed in the partitions. In some cases, the circularization and linearization is performed in the partitions. Linearization can be performed, e.g., with a restriction endonuclease that recognizes and cleaves within the donor oligonucleotide sequence.

The genomic nucleic acid fragments (e.g., circularized, linear, or linearized) can be mixed with one or more amplification primers, probes, enzymes, or a combination thereof, and then partitioned. Additionally, or alternatively, the genomic nucleic acid fragments (e.g., circularized, linear, or linearized) can be partitioned into mixture partitions that contain one or more amplification primer(s), probe(s), enzyme(s), or a combination thereof. Additionally, or alternatively, the genomic nucleic acid fragments (e.g., circularized, linear, or linearized, and optionally in combination with one or more amplification primer(s), probe(s), or enzyme(s)) can be partitioned into a plurality of mixture partitions, and then one or more amplification primer(s), probe(s), enzyme(s), or a combination thereof, can be introduced into the plurality of mixture partitions. Methods and compositions for delivering reagents (e.g., genomic fragments, probes, enzymes, primers, salts, buffers, divalent cations, etc.) to one or more mixture partitions include microfluidic methods as known in the art; droplet or microcapsule merging, coalescing, fusing, bursting, or degrading (e.g., as described in U.S. 2015/0027,892; US 2014/0227,684; WO 2012/149,042; and WO 2014/028,537); droplet injection methods (e.g., as described in WO 2010/151,776); and combinations thereof.

As described herein, the mixture partitions can be picowells, nanowells, or microwells. The mixture partitions can be pico-, nano-, or micro-reaction chambers, such as pico, nano, or microcapsules. The mixture partitions can be pico-, nano-, or micro-channels. The mixture partitions can be droplets, e.g., emulsion droplets.

Fragments of genomic nucleic acid (e.g., circularized, linear, or linearized), can be partitioned into any number of partitions. In general, the number of partitions is chosen to ensure that a minority of, a substantial minority of, few, substantially no, or no partitions contain multiple genomic nucleic acid fragments. Thus, the presence of multiple amplicons or detectable signals after amplification in a single partition can indicate that one or more detectable sequence elements were present in the same fragment. The number of partitions necessary to ensure adequate partitioning is dependent on a number of factors, including, but not limited to: (a) the size of the genome and/or number of genomes to be interrogated; (b) the method of fragmentation; (c) the number and size of genomic nucleic acid fragments generated; (d) the desired resolution of the double-stranded break point analysis; and (e) the desired statistical significance. In general, the number of partitions is at least about 500; 1000; 10000; or 20,000; 30,000; 50,000; or more.

In some embodiments, reagents such as genomic nucleic acid fragments (e.g., circularized, linear, or linearized), buffers, enzymes (e.g., polymerases for amplification and/or sequencing, ligase, or a combination thereof), substrates, nucleotides, probes, primers, salts, etc. are mixed together prior to partitioning, and then the sample is partitioned. In some cases, the reagents include a ligase and/or a polymerase and the sample is partitioned shortly after mixing reagents together so that substantially all, or the majority, of ligase and/or polymerase activity occurs after partitioning. In other cases, the reagents are mixed at a temperature in which the ligase and/or polymerase enzymes proceeds slowly, or not at all, the sample is then partitioned, and the reaction temperature is adjusted to allow the ligation and/or polymerase reaction to proceed. For example, the reagents can be combined on ice, at less than 5° C., or at 0, 1, 2, 3, 4, 5, 6, 7, 8, 9, 10, 11, 12, 13, 14, 15, 16, 17, 18, 19, 20, 20-25, 25-30, or 30-35° C. or more. In general, one of skill in the art will know how to select a temperature at which one or more ligase or polymerase enzymes are not active or are minimally active. In some cases, a combination of temperature and time are utilized to avoid substantial ligation and/or polymerization prior to partitioning.

In some cases, reagents can be mixed using one or more hot start ligases and/or polymerases, such as a hot start DNA-dependent DNA polymerase or a hot start ligase. Thus, genomic nucleic acid fragments, probes, buffers, salts, nucleotides, labels, enzymes, etc. can be mixed and then partitioned. Subsequently, the ligation and/or polymerization reaction, including multiple rounds of polymerization, and/or amplification can be initiated by heating the partition mixtures to activate the one or more hot-start enzymes.

Additionally, reagents can be mixed together without one or more reagents necessary to initiate an enzymatic reaction (e.g., polymerization, ligation, and/or amplification). The mixture can then be partitioned into a set of first partition mixtures and then the one or more essential reagents can be provided by fusing the set of first partition mixtures with a set of second partition mixtures that provide the essential reagent. Alternatively, the essential reagent can be added to the first partition mixtures without forming second partition mixtures. For example, the essential reagent can diffuse into the set of first partition mixture water-in-oil droplets. As another example, the missing reagent can be directed to a set of micro channels which contain the set of first partition mixtures.

In some embodiments, reagents can be mixed together to form a reaction mixture, and partitioned. Subsequently, one or more additional reagents can be added to the partitions. For example, one or more reagents can be injected into the partitions. In some cases, an electric field can be applied to an interface between a partition and a fluid to disrupt the interface and allow at least a portion of the fluid to enter the partition. As another example, one or more reagents can be directed to partitions in micro or nanoliter size wells via microfluidic techniques. Methods, compositions, and devices for injection of reagents into a partition can include, but are not limited to, those described in WO/2010/0151, 776.

Reagents that can be added by fusing partitions, injection, microfluidics or other means include but are not limited to ligation reagents (e.g., ligase), amplification reagents (e.g., one or more amplification primers or polymerases), detection reagents (e.g., intercalating dye or nucleic acid probe), sequencing reagents, or combinations thereof. As an example, DNA-dependent DNA polymerase (and, optionally, one or more primers) can be added into a partition to amplify the nucleic acid fragment in the partition, or a portion thereof.

In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes. In some cases, such stability or minimal coalescence is maintained for up to 4, 6, 8, 10, 12, 24, or 48 hours or more (e.g., at room temperature, or at about 0, 2, 4, 6, 8, 10, or 12° C.).

In some embodiments, the droplet is formed by flowing an oil phase through an aqueous sample comprising the genomic nucleic acid fragments to be detected. In some embodiments, the aqueous sample comprising the genomic nucleic acid fragments to be detected further comprises a buffered solution and an intercalating dye. In some embodiments, the aqueous sample comprising the genomic nucleic acid fragments to be detected further comprises a buffered solution, optionally an intercalating dye, and one or more probes for detecting one or more DNA sequence elements (e.g., an endogenous or heterologous DNA sequence element).

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H, 2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can be removed prior to heating, or left in place. The microcapsules can be resistant to coalescence and/or flocculation across a wide range of thermal and mechanical processing.

Following conversion of droplets into microcapsules, the microcapsules can be stored at about −70°, −20°, 0°, 3°, 4°, 5°, 6°, 7°, 8°, 9°, 10°, 15°, 20°, 25°, 30°, 35° or, 40° C. In some embodiments, these capsules are useful for storage or transport of partition mixtures. For example, samples can be collected at one location, partitioned into droplets containing enzymes, buffers, and/or primers or other probes, optionally one or more polymerization reactions can be performed, the partitions can then be heated to perform microencapsulation, and the microcapsules can be stored or transported for further analysis.

The microcapsule partitions can contain one or more probes (e.g., labeled probes as described herein) and can resist coalescence, particularly at high temperatures. Accordingly, the capsules can be incubated at a very high density (e.g., number of partitions per unit volume). In some embodiments, greater than 100,000, 500,000, 1,000,000, 1,500,000, 2,000,000, 2,500,000, 5,000,000, or 10,000,000 partitions can be incubated per mL. In some embodiments, the sample-probe incubations occur in a single well, e.g., a well of a microtiter plate, without inter-mixing between partitions. The microcapsules can also contain other components necessary for the incubation.

In some embodiments, the genomic nucleic acid fragments are partitioned into, or into at least, 500 partitions, 1000 partitions, 2000 partitions, 3000 partitions, 4000 partitions, 5000 partitions, 6000 partitions, 7000 partitions, 8000 partitions, 10,000 partitions, 15,000 partitions, 20,000 partitions, 30,000 partitions, 40,000 partitions, 50,000 partitions, 60,000 partitions, 70,000 partitions, 80,000 partitions, 90,000 partitions, 100,000 partitions, 200,000 partitions, 300,000 partitions, 400,000 partitions, 500,000 partitions, 600,000 partitions, 700,000 partitions, 800,000 partitions, 900,000 partitions, 1,000,000 partitions, 2,000,000 partitions, 3,000,000 partitions, 4,000,000 partitions, 5,000,000 partitions, 10,000,000 partitions, 20,000,000 partitions, 30,000,000 partitions, 40,000,000 partitions, 50,000,000 partitions, 60,000,000 partitions, 70,000,000 partitions, 80,000,000 partitions, 90,000,000 partitions, 100,000,000 partitions, 150,000,000 partitions, or 200,000,000 partitions.

In some embodiments, the genomic nucleic acid fragments are partitioned into a sufficient number of partitions such that all, substantially all, or at least a majority of partitions have no more than 5 genomic nucleic acid fragments (e.g., about 0.5, 1, 2, 3, 4, or 5 genomic nucleic acid fragment molecules). In some embodiments, the sample is partitioned into a sufficient number of partitions such that all, substantially all, or at least a majority of partitions have no more than 1 genomic nucleic acid fragment (e.g., about 0.05, 0.1, 0.2, 0.3, 0.4, 0.5, 0.75 or 1 genomic nucleic acid fragment molecule). In some embodiments, on average no more than 5, 4, 3, 2, 1, 0.75, 0.5, 0.4, 0.3, 0.2, 0.1, or 0.05 genomic nucleic acid fragment molecules are present in each partition. In some embodiments, on average about 0.05, 0.1, 0.2, 0.3, 0.4, 0.5, 0.75, 1, 2, 3, 4, or 5 genomic nucleic acid fragment molecules are present in each partition. In some embodiments, in a population of partitions containing genomic nucleic acid fragment molecules, the mode number of genomic nucleic acid fragment molecules in a partition is 1, or is 0.

In some embodiments, partitions contain excess detection reagents. For example, in some embodiments, partitions contain, on average, more than about 1 (e.g., 1, 2, 3, 4, 5, 6, 7, 8, 10, 12, 15, 20, 40, 50, 100, 150, 200, 250, 300, 350, 400, 500, 750, 1000 or more) primer, primer pairs, or probe molecules for detection of target DNA sequence elements (e.g., endogenous, exogenous, or heterologous DNA sequence elements), or a combination thereof. In some embodiments, multiple detection reagents for detection of multiple target DNA sequence elements are present in the partitions. For example, 1, 2, 3, 4, 5, 6, 7, 8, 9, 10 or more different target DNA sequence elements can be detected in one or more partitions.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

d) Amplifying

Amplification is performed to selectively amplify the fragments containing the inserted donor polynucleotide. This is achieved by use of a pair of primers that are oriented "away" ($\leftarrow$ $\rightarrow$) from each other in the inserted donor polynucleotide, but that due to circularization of the fragment are able to amplify the sequence formed by circularization. Linearization of the circularized fragments by cleaving the inserted donor polynucleotide can retain amplifiability provided by the circularization. This method is a variant of what is sometimes referred to as "inverse" or "inverted PCR."

"Amplifying" refers to a step of submitting a solution (e.g., a solution in a mixture partition) to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential"

increase in target nucleic acid. However, "amplifying" as used herein can also refer to linear increases in the numbers of a select target sequence of nucleic acid, such as is obtained with cycle sequencing or linear amplification.

The term "amplification reaction" refers to any in vitro means for multiplying the copies of a target sequence of nucleic acid in a linear or exponential manner. Such methods include but are not limited to polymerase chain reaction (PCR); DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3 SR); isothermal amplification reactions (e.g., single-primer isothermal amplification (SPIA)); as well as others known to those of skill in the art.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. A pair of amplification primers can be configured to hybridize to opposite strands of an inserted exogenous donor oligonucleotide, or fragment thereof, wherein the hybridized pair of primers are oriented such that their 5' ends are proximal and their 3' ends are distal prior to circularization of the fragment.

Figure 6:
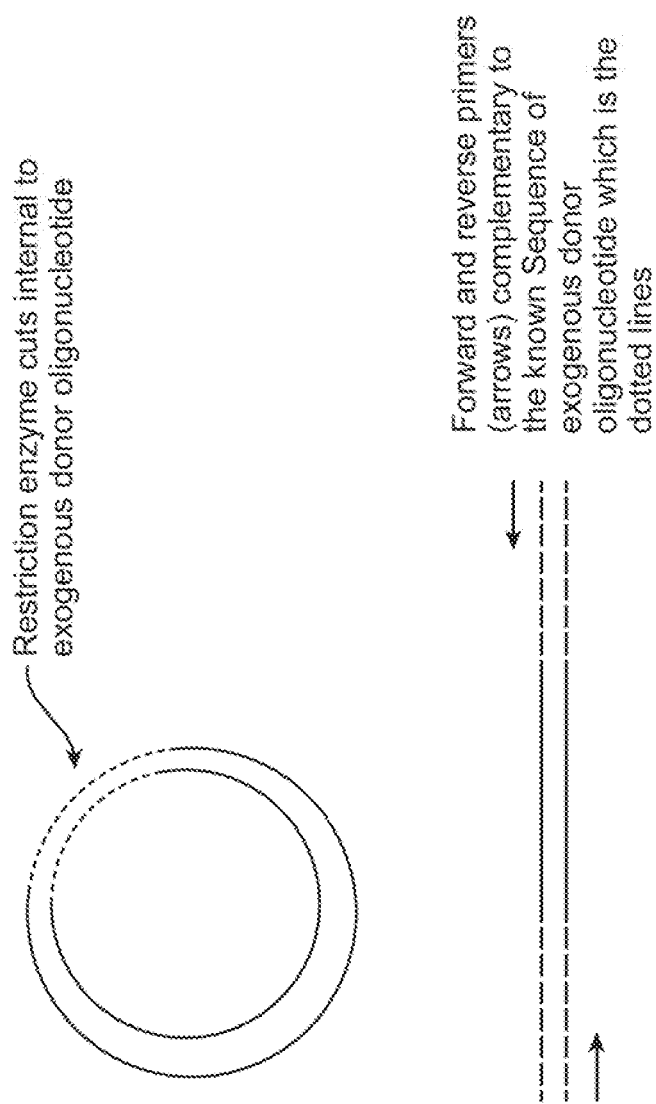
FIG. 6: depicts an alternative embodiment, in which circularized fragments are cut with a restriction enzyme that cleaves a sequence within the exogenous donor oligonucleotide. Forward and reverse primers (arrows) complementary to the known sequence of exogenous donor oligonucleotide (dotted lines) enable selective amplification of genomic fragments containing the exogenous donor oligonucleotide. Linearization can be performed in the initial partition, or after partitions have been combined (e.g., droplets broken). In some cases, linearized fragments can be re-partitioned.

Upon circularization, the 5' ends remain relatively closer (more proximal) as compared to the 3' ends of the primers, and the region flanked by the primers (generated by circularization) can be amplified. After circularization, fragments containing an inserted donor polynucleotide can be linearized by selective cleavage of the donor polynucleotide sequence (see, e.g., FIG. 6). The orientation of the primers hybridized to the linearized fragment containing an inserted and cleaved donor polynucleotide can be inverted as compared to the initial or circularized fragments. Thus, the primers can be configured to hybridize to opposite strands of a portion of the inserted and cleaved exogenous donor oligonucleotide, or fragment thereof, wherein the hybridized pair of primers are oriented such that their 5' ends are distal and their 3' ends are proximal.

Figure 5:
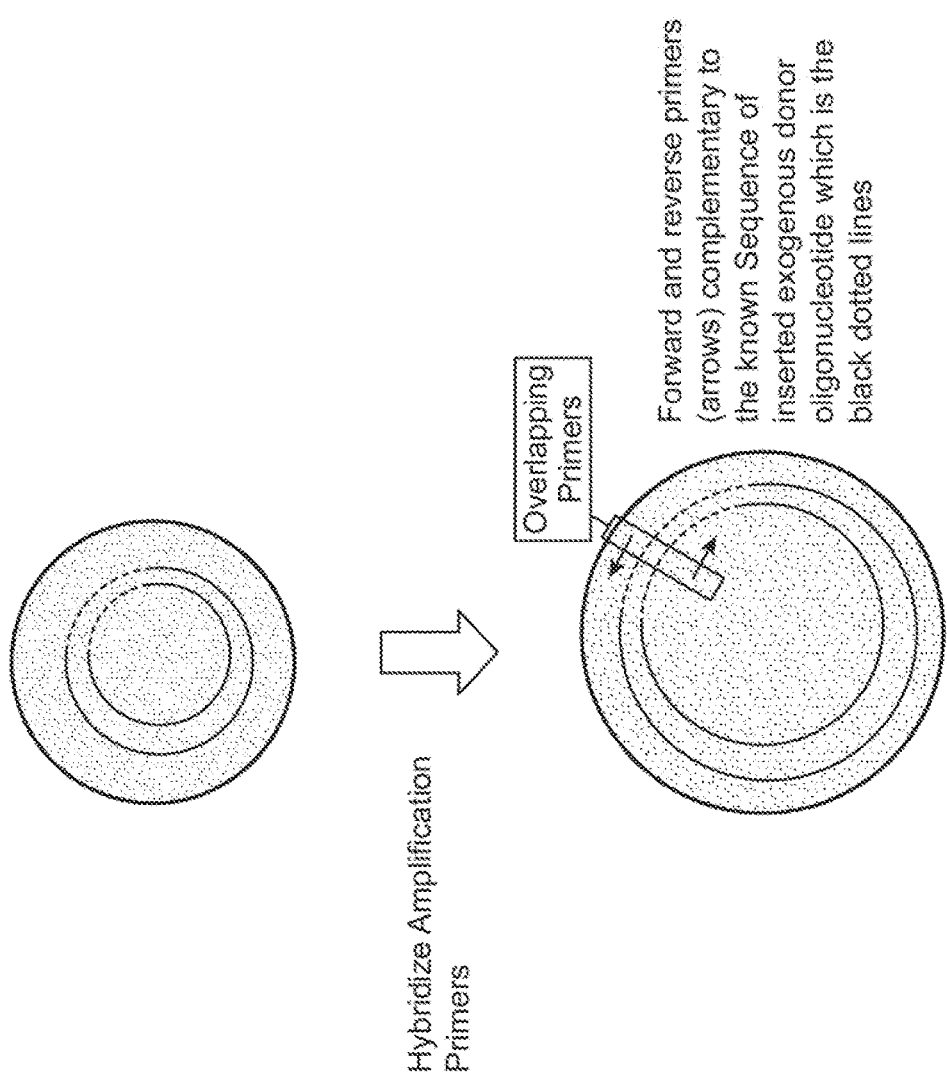
FIG. 5: depicts an embodiment of a portion of a quantitative assay for double stranded break points in a genome of a cell. In this embodiment, partitions containing circularized genomic DNA fragments containing an inserted exogenous donor oligonucleotide are subject to amplification conditions with overlapping amplification primers. The primers hybridize to opposite strands of the target sequence with their 5' ends are overlapping.

In some cases, the 5' ends of the pair of primers hybridized to opposite strands of a circularized or linearized genomic nucleic acid fragment having an inserted exogenous donor oligonucleotide, or fragment thereof, overlap by, or by about, 1, 2, 3, 4, 5, 6, 7, 8, 9, 10, 11, 12, 13, 14, 15, 16, 17, 18, 19, or 20 nucleotides (see, e.g., FIG. 5). In some cases, one or more primers are labeled (e.g., detectably labeled).

Amplification can be performed with a primer or pair of primers that hybridize (e.g., specifically or stringently hybridize) to an inserted donor polynucleotide sequence. The primer or primers can be configured to provide an amplification product in the presence of a circularized or subsequently linearized genomic nucleic acid fragment containing an inserted exogenous donor oligonucleotide or fragment thereof and suitable amplification reagents, under conditions suitable for amplification. For example, a pair of amplification primers can be configured to be complementary to opposite strands of the donor polynucleotide or portion thereof, and are oriented such that the 5' ends are proximal to each other and the 3' ends are distal to each other when hybridized to the initial genomic nucleic fragment containing the inserted donor polynucleotide or portion thereof Amplification can be performed in the presence of an intercalating dye that provides a detectable signal in the presence of double stranded nucleic acid. Thus, in partitions in which amplification successfully generates amplicons, the intercalating dye will increase in fluorescence and provide a detectable signal indicating the presence of a genomic nucleic acid fragment containing an inserted exogenous donor polynucleotide in that partition. Alternatively, the intercalating dye can be delivered to the partition to detect the presence or absence of genomic nucleic acid fragments containing an inserted exogenous donor polynucleotide and/or amplicons thereof. The intercalating dye can be used to detect a total amount of on-target and off-target genome editing, or detect a total amount of double strand break points induced by a genome editing reagent or exogenous insult.

Amplification can be performed in the presence of a probe that specifically detects the presence of a target nucleic acid sequence. For example, amplification can be performed in the presence of a labeled probe that specifically detects an target nucleic acid sequence endogenous to the genome of a cell. In partitions that contain a genomic nucleic acid fragment having that endogenous sequence, the amplification will result in a detectable signal indicating the presence of the endogenous sequence. As another example, the amplification can be performed in the presence of a labeled probe that specifically detects a target nucleic acid sequence heterologous to the genome of a cell. In some cases, the heterologous sequence is generated by circularizing a genomic acid fragment. In partitions that contain a genomic acid fragment (e.g., circularized or linearized) having that heterologous sequence, the amplification will result in a detectable signal indicating the presence of that heterologous sequence.

e) Detecting and Quantifying

In some embodiments, the presence or absence of a genomic nucleic acid fragment containing an inserted exogenous donor oligonucleotide is detected in a partition, or a plurality of partitions. The presence of a genomic nucleic acid fragment containing an inserted exogenous donor oligonucleotide in a partition indicates that the genomic DNA contained a double stranded break point in the cell from which it is derived. In some cases, the frequency or number of genomic nucleic acid fragments containing an inserted exogenous donor oligonucleotide that are detected in a partition indicates the frequency or number of double stranded break points in the genome(s) of the cell or population of cells from which the fragments are derived.

Figure 2:
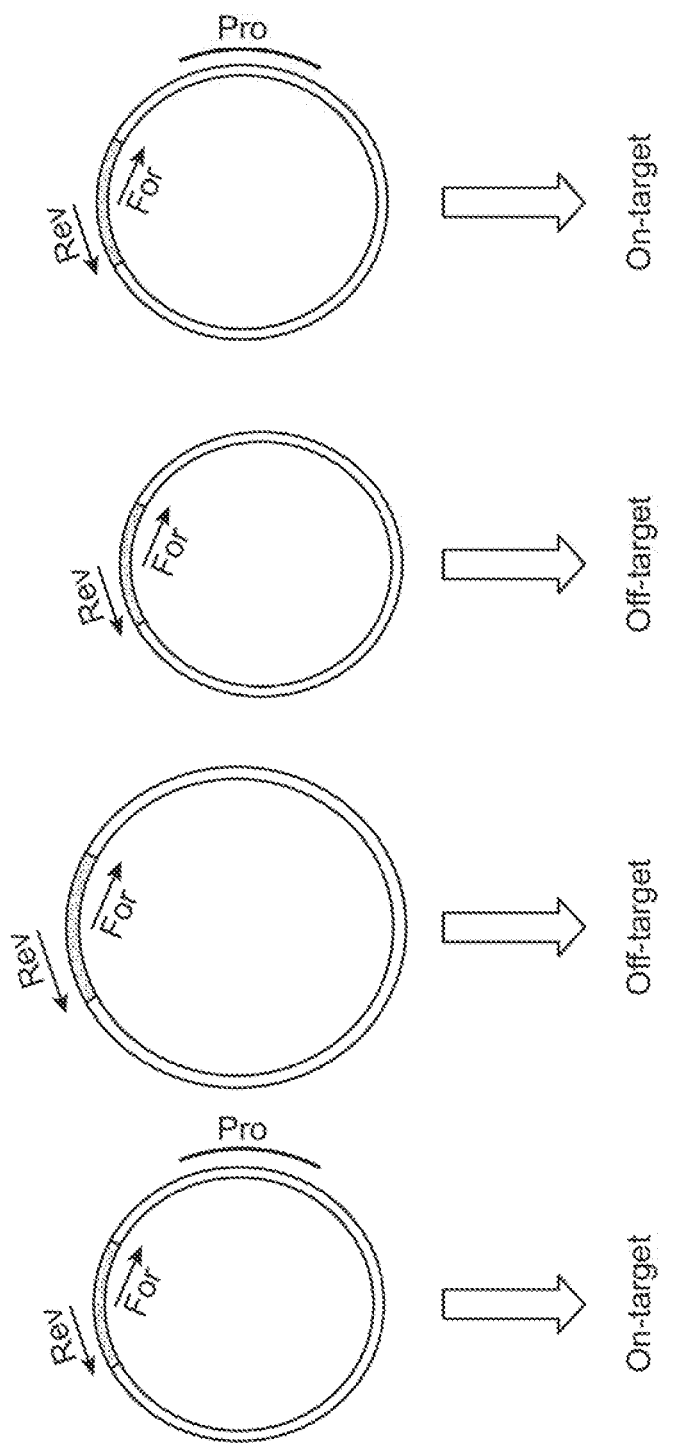
FIG. 2: depicts various amplification and detection schemes for detecting off-target genome cleavage by a genome editing reagent, on-target cleavage by a genome editing reagent, or a combination thereof. Rev and For indicate reverse and forward amplification primers respectively. Pro indicates a probe that selectively detects a sequence proximal to an on-target genome editing reagent cleavage site.

A digital readout assay, e.g., digital analysis, can be used to count the frequency that an inserted exogenous donor oligonucleotide or fragment thereof is in a genome or population of genomes. Thus, the frequency of double stranded breaks that were in the genome or genomes can be determined. The frequency can be determined by detecting the frequency of partitions containing an amplicon as described herein (see, e.g., FIG. 2). Generally, the process of digital analysis involves determining for one or more partitions of a sample whether the partition is positive or negative (e.g., above or below a cut-off value for signal) for the presence of the genomic fragment in which an exogenous donor oligonucleotide has been inserted.

In some embodiments, a partition is "positive" for the presence of the genomic fragment in which an exogenous donor oligonucleotide has been inserted if an amplified product of at least a portion of such a fragment is detected in the partition. In some embodiments, the amplified product is detected by detecting the presence of a signal generated by an intercalating dye that increases in fluorescence as amplified product is generated. In some embodiments, the amplified product is detected by detecting the presence of a signal generated by label linked to a probe (e.g., a fluorescent, chemiluminescent, radioactive, or enzymatic label linked to a probe, such as an oligonucleotide, protein, peptide, or an aptamer probe). In some embodiments, two or more probes are detected in the partition by detecting the production of a signal that is generated when two labeled probes are present in the same partition but not in the absence of one or both probes from the same partition. In some embodiments, a partition is "negative" for the presence of the target molecule if no amplified product of a genomic fragment containing an inserted exogenous donor oligonucleotide or portion thereof acid is detected.

In some embodiments, the methods further comprise, e.g., as a control, such as a normalization control, specific detection of an endogenous and/or heterologous polynucleotide sequence in a mixture partition. For example, amplification can be performed in the presence of a labeled probe that specifically detects a control nucleic acid sequence endogenous to the genome of a cell. In partitions that contain a genomic nucleic acid fragment having that endogenous control sequence, the amplification will result in a detectable signal indicating the presence of the endogenous sequence.

As another example, the amplification can be performed in the presence of a labeled probe that specifically detects a control nucleic acid sequence heterologous to the genome of a cell. In some cases, the heterologous sequence is generated by circularizing a genomic nucleic acid fragment, whereby the circularizing generates a continuous nucleotide sequence that is not present in the intact genome of the cell. In partitions that contain a genomic nucleic acid fragment (e.g., circularized or circularized and then linearized) having that heterologous sequence, the amplification will result in a detectable signal indicating the presence of that heterologous sequence. As described herein, detection of this sequence can, e.g., be used to control for ligation efficiency.

The endogenous and/or heterologous sequences and detection thereof can be used as a reference or normalization signal. In some cases, the endogenous sequence can be used as a reference or normalization signal to indicate the efficiency of the assay. For example, a known number of cells can be evaluated for the presence or quantity of double strand break points by contacting the cells with an exogenous donor oligonucleotide under conditions suitable to insert the exogenous donor oligonucleotide into double strand break points in the genome of the cells, extracting genomic nucleic acid, fragmenting, partitioning and circularizing (e.g., circularizing before or after partitioning), optionally linearizing (e.g., before or after partitioning), and then detecting partitions containing a circular or linearized genomic nucleic acid fragment having an inserted exogenous donor oligonucleotide, or a portion thereof, as described herein. Partitions containing an endogenous reference sequence that is present in the genome of the cells can also be detected. The presence or quantity of partitions in which the endogenous reference sequence is detected can indicate that the assay has been performed successfully. The number of partitions in which the endogenous reference sequence is detected can also indicate a value that is proportional to the number of genomes used in the assay. This can be used to normalize the number of partitions in which a genomic nucleic acid fragment having an inserted exogenous donor oligonucleotide, or fragment thereof, is detected. This normalization factor can be used to determine an absolute quantitation for the number of inserted donor oligonucleotides in the population of genomes (and cells from which the genomes are derived) examined, and thus infer a quantity or frequency of double stranded break points in the genomes of the cells.

Similarly, partitions containing a heterologous reference sequence that is not present in the genome of the cell, but is generated by circularizing (and optionally subsequently linearizing) a genomic nucleic acid fragment can also be detected. The number of partitions containing the heterologous reference sequence can be compared to the number of partitions containing the endogenous reference sequence. The existence or quantity of partitions containing the heterologous reference sequence generated by circularization as compared to the endogenous reference sequence can be used to indicate the efficiency of the circularization step. The existence or quantity of partitions in which the endogenous and/or heterologous reference sequences are detected can also indicate that the assay has been performed successfully.

In some cases, partitions containing an exogenous control polynucleotide can be detected. For example, a plurality of genomic nucleic acid fragments (e.g., before or after circularizing and/or linearizing) can be mixed with a known amount of a control polynucleotide and then partitioned. Detection and counting of partitions containing the control polynucleotide can indicate that the partitioning and/or detection is performed successfully, allow for normalization of resulting data and thus absolute quantitation, and the like.

In some embodiments, partitions containing a genomic fragment having a sequence proximal to a genome editing reagent cleavage site can be detected, e.g., using a probe that specifically detects the proximal sequence. The sequence proximal to a genome editing cleavage site can be within about 1; 2; 3; 4; 5; 6; 7; 8; 9; 10; 12; 14; 15; 18; 20; 22; 25; 30; 35; 40; 45; 50; 60; 70; 80; 90; 100; 125; 150; 175; 225; 250; 300; 325; 350; 375; 400; 425; 450; 475; 500; 550; 600; 650; 700; 750; 1,000 base pairs or kilobase pairs from the genome editing cleavage site. Similarly, partitions containing a genomic fragment having an inserted exogenous donor oligonucleotide, or portion thereof, and a sequence proximal to a genome editing reagent cleavage site can be detected.

In some cases, the proximal sequence and the donor oligonucleotide (or fragment thereof) sequence are detected by a single probe (e.g., a probe that detects a sequence generated by insertion of the donor oligonucleotide into a genome editing reagent target site). For example, the probe can, at least in part, hybridize to a junction sequence formed by the insertion. In some cases, the proximal sequence and the donor oligonucleotide (or fragment thereof) are detected by two probes. In some cases, the presence of the donor oligonucleotide in the genomic fragment is detected by detecting amplification of at least a portion of the genomic fragment with an intercalating dye, wherein the amplification is performed using primers that hybridize to at least a portion of the inserted donor oligonucleotide. In some cases, the amplification is performed on a circularized or linearized genomic nucleic acid fragment. In such an embodiments, the presence of a sequence proximal to a genome editing reagent site can be detected, e.g., with a probe that specifically hybridizes to at least a portion of the sequence proximal to a genome editing reagent site.

In some cases, partitions containing both a sequence proximal to a genome editing reagent cleavage site and an inserted exogenous donor oligonucleotide, or portion thereof, can be detected and/or quantitated. In some cases, partitions containing a genomic fragment having a sequence proximal to a genome editing reagent cleavage site but lacking an inserted exogenous donor oligonucleotide, or portion thereof, can be detected and/or quantitated. In some cases, partitions containing an inserted exogenous donor oligonucleotide, or portion thereof, but lacking a genomic fragment having a sequence proximal to a genome editing reagent cleavage site can be detected and/or quantitated.

The detection and/or quantitation of partitions containing a genomic fragment with an inserted exogenous donor oligonucleotide, or fragment thereof, and a sequence proximal to a genome editing reagent cleavage site can thereby indicate a number or frequency of on-target genome editing. The detection and/or quantitation of partitions containing a genomic fragment having a sequence proximal to a genome editing reagent cleavage site but lacking an inserted exogenous donor oligonucleotide, or portion thereof, can thereby indicate a number or frequency of genome editing reagent cleavage sites that have not been successfully edited. The detection and/or quantitation of partitions containing an inserted exogenous donor oligonucleotide, or portion thereof, but lacking a genomic fragment having a sequence proximal to a genome editing reagent cleavage site can thereby indicate a number or frequency of off-target genome cleavage by the genome editing reagent. In some cases, the number or frequency of the indicated on-target genome editing is compared to the number or frequency of the indicated off-target genome editing, thereby indicating a rate of on-target genome editing as compared to off-target genome editing.

Accordingly, in some embodiments, methods described herein can include comparing a ratio of i) to ii), wherein i) is a number of mixture partitions containing an amplicon and a sequence proximal to an on-target genome-editing reagent cleavage site; and ii) is a number of mixture partitions containing an amplicon, thereby determining a rate of on-target genome editing by a genome editing reagent or method. Similarly, the methods described herein can include counting the number of mixture partitions that contain an amplicon and do not contain a sequence proximal to an on-target genome-editing reagent cleavage site, thereby detecting a number of off-target genome insertions. Moreover, the methods described herein can include comparing the ratio of i) to ii), wherein: i) is a number of mixture partitions that contain an amplicon and do not contain a sequence proximal to an on-target genome-editing reagent cleavage site; and ii) is a number of mixture partitions containing an amplicon, thereby determining a rate of off-target genome insertions by a genome editing reagent or method.

Figure 3:
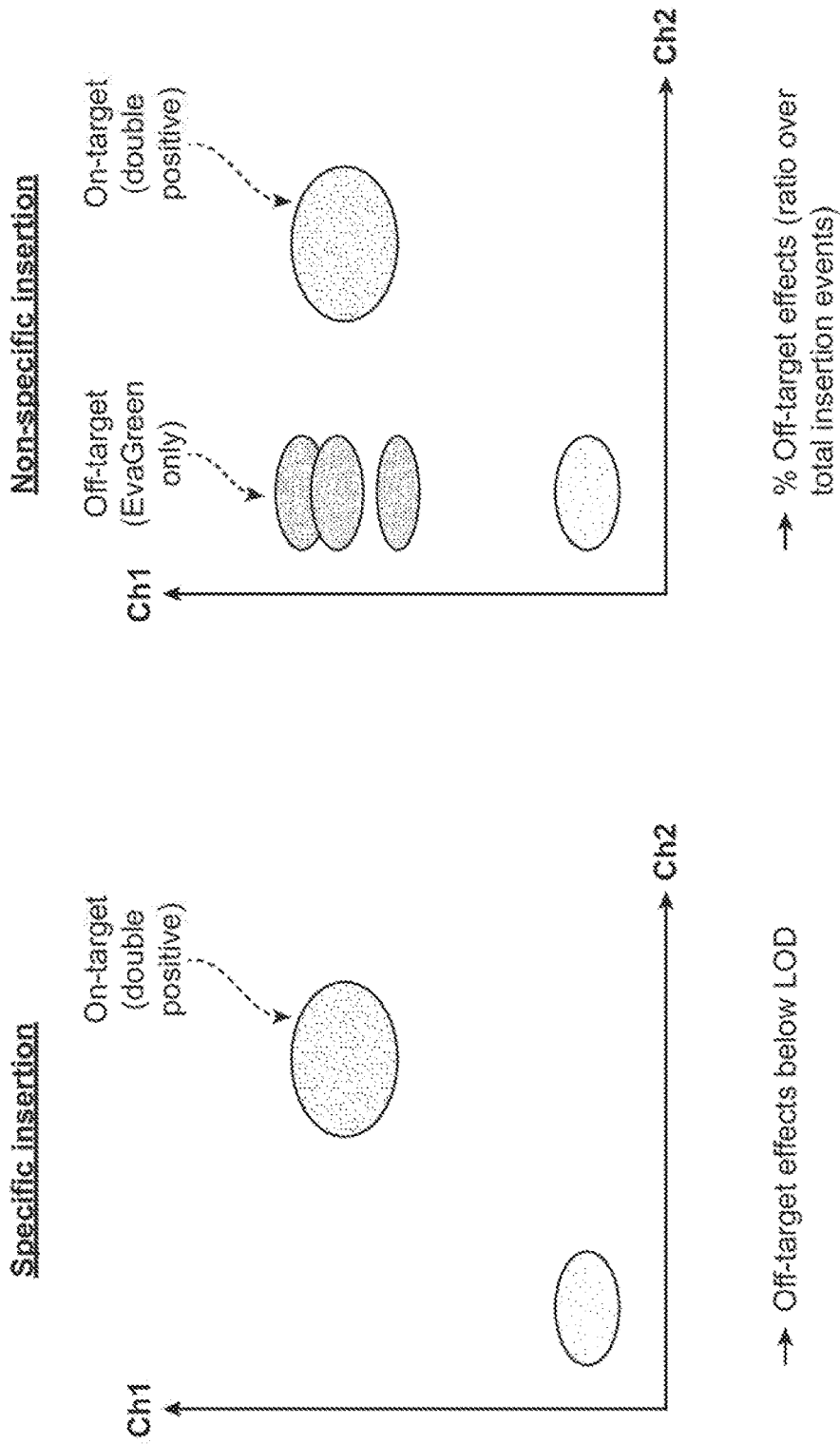
FIG. 3: is an illustration of data that can be provided in a partition based assay for detection of off-target and on-target genome editing. In this embodiment, double positive partitions exhibit a positive signal for amplification of a fragment containing a dsODN (e.g., as detected by intercalating dye) in a first detection channel (Ch1). Double positive partitions can exhibit a different positive signal if the fragment also contains a sequence proximal to an on-target genome editing reagent cleavage site (e.g., as detected by nucleic acid probe) in a second detection channel (Ch2). The presence of positive signals in both detection channels can indicate on-target insertion of the dsODN and therefore on-target editing. Single positive partitions can exhibit a positive signal for amplification of a fragment containing the dsODN (e.g., as detected by intercalating dye) in the first detection channel, but lack a positive signal for sequence proximal to an on-target genome editing reagent cleavage site. Such single positive partitions correspond to off-target cleavage and/or edit sites.

In some embodiments, the detection and/or quantitation is performed in a device that can distinguish two or more (e.g., 2, 3, 4, 5, 6, 7, 8, 9, 10, 11, 12, 13, 14, 15, or more) distinguishable signals. Thus, e.g., fragments containing an inserted donor polynucleotide, or amplicons thereof, can be detected on one channel via an intercalating dye. Additional channels of the device can be used to simultaneously detect a sequence proximal to an on-target genome-editing reagent cleavage site, and/or one or more of the foregoing control sequences, such as an endogenous reference sequence, a heterologous sequence generated by circularization, an exogenous control polynucleotide, or a combination thereof (see, e.g., FIG. 3).

In some cases, a cell, cell line, or population of cells can be assayed as described herein without having been contacted with a genome editing reagent to determine a basal rate of double strand breakage and/or a basal rate of donor oligonucleotide insertion. The basal rate can be used to normalize an assay of a cell, cell line, or population of cells that has been contacted with a genome editing reagent. Alternatively, a cell, cell line, or population of cells can be assayed as described herein without having been contacted with a genome editing reagent to assess exposure to an exogenous insult (e.g., a chemical mutagen, intense magnetic field, or ionizing radiation).

In some cases, a cell, cell line, or population of cells can be contacted with a donor oligonucleotide without exposure or substantial exposure to an exogenous insult (e.g., a chemical mutagen, intense magnetic field, or ionizing radiation) and/or without contacting with a genome editing reagent. Insertion of the donor oligonucleotide into double strand breaks can be assayed using the methods described herein to determine a basal number of double strand break points and/or a basal rate of double strand break point insertion. The basal rate can be used to normalize one or more of the assays described herein.

In some embodiments, the method of detection comprises fluorescence detection. Methods of detecting accumulated amplification product using fluorescence are well known in the art. Examples of suitable approaches include, for example the use of intercalating dye, the use of labeled probes in conjunction with 5' nuclease cleavage, and the use of structured probes.

The use of intercalating dyes utilizes fluorogenic compounds that bind to double stranded DNA. In this type of approach, amplification product (which in some cases is double stranded) binds dye molecules in solution to form a complex. With the appropriate dyes, it is possible to distinguish between dye molecules remaining free in solution and dye molecules bound to amplification product. For example, certain dyes fluoresce efficiently only when bound to double stranded DNA, such an amplification product. Examples of such dyes include, but are not limited to, SYBR Green and Pico Green (from Molecular Probes, Inc., Eugene, Oreg.), ethidium bromide, propidium iodide, chromomycin, acridine orange, Hoechst 33258, TOTO-I, YOYO-1, and DAPI (4',6-diamidino-2-phenylindole hydrochloride). Additional description regarding the use of intercalation dyes is provided, e.g., by Zhu et al., *Anal. Chem.* 66:1941-1948 (1994).

In some embodiments, the intercalating dyes can be used to discriminate between partitions that do and do not contain a genomic nucleic acid fragment having an inserted exogenous donor oligonucleotide, or fragment thereof. In some cases, intercalating dyes can be used to discriminate between single positive, double-positive, and multiply positive partitions (e.g., positive for 3, 4, 5, or more structurally different genomic nucleic acid fragments having an inserted exogenous donor oligonucleotide, or fragment thereof). For example, in some cases, partitions containing 2 or more different target sequences, and an intercalating dye that detects the amplicons of such target sequences, can provide a greater detectable signal than partitions containing only one target sequence amplicon. Similarly partitions containing only 1 target sequence amplicon, and an intercalating dye, can provide a higher detectable signal than partitions containing no target sequence amplicon. As yet another example, the concentrations of primers for amplification of specific target sequences can be varied to alter the amount of amplicon generated in an end-point amplification (e.g., PCR) reaction. Thus, the detection with an intercalating dye can distinguish between the presence or absence of different target sequence amplicons on the basis of signal intensity. Methods, compositions, and devices for multiplex detection of target sequence amplicons, can be found, e.g., in McDermott, et al. Anal. Chem., 2013, 85 (23), pp 11619-11627; and US/2014/0178889.

Fluorogenic nuclease assays are another example of an amplification product quantification method that can be used successfully with the devices and methods described herein. The basis for this method of monitoring the formation of amplification product is to measure amplicon accumulation using a dual-labeled fluorogenic oligonucleotide probe, an approach frequently referred to in the literature as the "TaqMan" method.

The probe used in such assays can be a short (e.g., approximately 20-25 bases in length) polynucleotide that is labeled with two different fluorescent dyes or one fluorescent dye and one non-fluorescent quenching moiety. In some cases, the 5' terminus of the probe can be attached to a reporter dye and the 3' terminus attached to a fluorescent or non-fluorescent quenching moiety. In other cases, the dyes can be attached at other locations on the probe. The probe can be designed to have at least substantial sequence complementarity with the probe-binding site on the target nucleic acid (e.g., substantial sequence complementarity with at least a portion of an endogenous or heterologous reference sequence, sequence proximal to a genome editing cleavage site, or sequence proximal to an on-target genome editing cleavage site). Upstream and downstream PCR primers that bind to regions that flank the probe binding site can also be included in the reaction mixture. When the fluorogenic probe is intact, energy transfer between the fluorophore and quencher moiety occurs and quenches emission from the fluorophore. During the extension phase of PCR, the probe is cleaved, e.g., by the 5' nuclease activity of a nucleic acid polymerase such as Taq polymerase, or by a separately provided nuclease activity that cleaves bound probe, thereby separating the fluorophore and quencher moieties. This results in an increase of reporter emission intensity that can be measured by an appropriate detector. Additional details regarding fluorogenic methods for detecting PCR products are described, for example, in U.S. Pat. No. 5,210,015 to Gelfand, U.S. Pat. No. 5,538,848 to Livak, et al., and U.S. Pat. No. 5,863,736 to Haaland, each of which is incorporated by reference in its entirety, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 4 88:7276-7280, (1991); and Livak, K. J., et al., PCR Methods and Applications 357-362 (1995).

Structured probes (e.g., "molecular beacons") provide another method of detecting accumulated amplification product. With molecular beacons, a change in conformation of the probe as it hybridizes to a complementary region of the amplified product results in the formation of a detectable signal. In addition to the target-specific portion, the probe includes additional sections, generally one section at the 5' end and another section at the 3' end, that are complementary to each other. One end section is typically attached to a reporter dye and the other end section is usually attached to a quencher dye. In solution, the two end sections can hybridize with each other to form a stem loop structure. In this conformation, the reporter dye and quencher are in sufficiently close proximity that fluorescence from the reporter dye is effectively quenched by the quencher. Hybridized probe, in contrast, results in a linearized conformation in which the extent of quenching is decreased. Thus, by monitoring emission changes for the reporter dye, it is possible to indirectly monitor the formation of amplification product. Probes of this type and methods of their use is described further, for example, by Piatek, A. S., et al., Nat. Biotechnol. 16:359-63 (1998); Tyagi, S. and Kramer, F. R., Nature Biotechnology 14:303-308 (1996); and Tyagi, S. et al., Nat. Biotechnol. 16:49-53 (1998).

In some embodiments, a detector that is capable of detecting a signal or multiple signals is used to analyze each partition for the presence or absence of the target molecule. For example, in some embodiments a one or two-color reader (e.g., fluorescence detector) is used. The fraction of positive-counted partitions can enable the determination of absolute concentrations, or relative concentrations, for the DNA sequence elements (e.g., genomic nucleic acid fragments having an inserted exogenous donor oligonucleotide or portion thereof) to be detected. In some cases, the fraction of positive-counted partitions can enable the determination of the relative or absolute frequency with which a cell or population of cells has double stranded break points, has been successfully edited at a target site, and/or contains off-target edited sites.

Once a binary "positive or negative" result has been determined for each of the partitions of the sample, the data for the partitions can be analyzed using an algorithm based on Poisson statistics to quantify the amount of double stranded break points in the genome of the cell or population of cells from which the partitioned, fragmented, circularized, and optionally subsequently linearized fragments are derived. Statistical methods for quantifying the concentration or amount of a target molecule or target molecules are described, for example, in WO 2010/036352, which is incorporated by reference herein in its entirety. Similar algorithms can be used to analyze assays in which double positive, single positive (+− or −+), or double negative results are observed or obtainable.

In some cases, the number and/or frequency of "positive" or "yes" and "no" partitions can be adjusted by an efficiency factor to account for an expected efficiency of successful exogenous donor oligonucleotide insertion. The efficiency factor can be a constant. For example, it can be empirically determined or assumed that exogenous donor oligonucleotides are successfully inserted only, only about, or at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or more of the time a double strand break or genome editing reagent cleavage product is present or generated. An efficiency factor can therefore be applied to adjust assay data accordingly to determine an absolute number or frequency of double strand break points, on-target genome edits, off-target genome edits, or a combination thereof. Alternatively, the efficiency factor can be assumed, determined, or further adjusted based on assay conditions. For example, the efficiency factor can be adjusted based on the genome editing reagent or donor oligonucleotide used in an experiment. For example, if under the conditions employed in an assay, insertion of exogenous donor oligonucleotide is expected to occur in about 50% of double stranded break points, then the detected rate of exogenous donor oligonucleotide insertion can be multiplied by 2 to adjust for this expected efficiency and obtain absolute double stranded break point quantification.

II. Compositions

Described herein is an exogenous donor oligonucleotide. The exogenous donor oligonucleotide can be single stranded or double stranded. In some cases, the exogenous donor oligonucleotide, or a portion thereof, is double stranded. In some cases, the exogenous donor oligonucleotide is double stranded and has one or more 5' and/or 3' single stranded (e.g., sticky) ends. In some cases, the exogenous donor oligonucleotide is double stranded with blunt 5' and/or 3' ends. The exogenous donor oligonucleotide can be DNA, RNA, or a combination thereof. In some cases, the exogenous donor oligonucleotide is DNA. In some cases, the exogenous donor oligonucleotide is phosphorylated (e.g., 5' and/or 3' phosphorylated). In some cases, the exogenous donor oligonucleotide is 5' phosphorylated.

The exogenous donor oligonucleotide can contain one or more nucleotide linkages that are different from a naturally occurring phosphodiester bond between nucleotide bases. In some cases, the exogenous donor oligonucleotide contains one or more modifications (e.g., base modifications, or modifications of one or more phosphodiester bonds between bases) that increase the in vivo stability or decrease in vivo degradation (e.g., nuclease digestion) of the exogenous donor oligonucleotide or fragment thereof.

The exogenous donor oligonucleotide can contain one or more phosphorothioate linkages. In some cases, the exogenous donor oligonucleotide contains a phosphorothioate linkage between a 5' ultimate nucleotide and a 5' penultimate nucleotide. In some cases, the exogenous donor oligonucleotide can contain, or can further contain, a phosphorothioate linkage between a 5' penultimate nucleotide and a 5' antepenultimate nucleotide. In some cases, the exogenous donor oligonucleotide can contain, or can further contain, a phosphorothioate linkage between a 5' antepenultimate nucleotide and a 5' preantepenultimate nucleotide. In some cases, one or more of the foregoing 5' phosphorothioate linkages are on one strand of a double stranded exogenous donor oligonucleotide. In some cases, one or more of the foregoing 5' phosphorothioate linkages are on different strands of a double stranded exogenous donor oligonucleotide. In some cases, one or more of the foregoing 5' phosphorothioate linkages are on opposite strands of a double stranded exogenous donor oligonucleotide.

In some cases, the exogenous donor oligonucleotide contains a phosphorothioate linkage between a 3' ultimate nucleotide and a 3' penultimate nucleotide. In some cases, the exogenous donor oligonucleotide can contain, or can further contain, a phosphorothioate linkage between a 3' penultimate nucleotide and a 3' antepenultimate nucleotide. In some cases, the exogenous donor oligonucleotide can contain, or can further contain, a phosphorothioate linkage between a 3' antepenultimate nucleotide and a 3' preantepenultimate nucleotide. In some cases, one or more of the foregoing 3' phosphorothioate linkages are on one strand of a double stranded exogenous donor oligonucleotide. In some cases, one or more of the foregoing 3' phosphorothioate linkages are on different strands of a double stranded exogenous donor oligonucleotide. In some cases, one or more of the foregoing 3' phosphorothioate linkages are on opposite strands of a double stranded exogenous donor oligonucleotide.

In some cases, the exogenous donor oligonucleotide contains a combination of one or more of the foregoing 5' and/or 3' phosphorothioate linkages. For example, the exogenous donor oligonucleotide can be a double stranded exogenous donor oligonucleotide that contains one, two, or three of the foregoing 5' phosphorothioate linkages on one, both, or different strands. As another example, the exogenous donor oligonucleotide can be a double stranded exogenous donor oligonucleotide that contains one, two, or three of the foregoing 3' phosphorothioate linkages on one, both, or different strands. As yet another example, the exogenous donor oligonucleotide can be a double stranded exogenous donor oligonucleotide that contains one, two, or three of the foregoing 5' phosphorothioate linkages on one, both, or different strands and one, two, or three of the foregoing 3' phosphorothioate linkages on one, both, or different strands.

In some cases, the exogenous donor oligonucleotide is a double stranded oligonucleotide having two 5' phosphorylated and blunt ends with phosphorothioate linkages between the 5' ultimate and 5' penultimate nucleotide and between the 5' penultimate and 5' antepenultimate nucleotide of one strand. In some cases, the exogenous donor oligonucleotide is a double stranded oligonucleotide having two 5' phosphorylated and blunt ends with phosphorothioate linkages between the 5' ultimate and 5' penultimate nucleotide and between the 5' penultimate and 5' antepenultimate nucleotide of both strands. In some cases, the exogenous donor oligonucleotide is a double stranded oligonucleotide having two 5' phosphorylated and blunt ends with phosphorothioate linkages between the 3' ultimate and 3' penultimate nucleotide and between the 3' penultimate and 3' antepenultimate nucleotide of one strand.

In some cases, the exogenous donor oligonucleotide is a double stranded oligonucleotide having two 5' phosphorylated and blunt ends with phosphorothioate linkages between the 3' ultimate and 3' penultimate nucleotide and between the 3' penultimate and 3' antepenultimate nucleotide of both strands. In some cases, the exogenous donor oligonucleotide is a double stranded oligonucleotide having two 5' phosphorylated and blunt ends with a phosphorothioate linkage between the ultimate and penultimate nucleotides at both the 5' and 3' ends of one or both strands. In some cases, the exogenous donor oligonucleotide is a double stranded oligonucleotide having two 5' phosphorylated and blunt ends with a phosphorothioate linkage between the ultimate and penultimate nucleotides and between the penultimate and antepenultimate nucleotides at both the 5' and 3' ends of one or both strands.

In some cases, the exogenous donor oligonucleotide is a double stranded oligonucleotide, such as any of the foregoing double stranded exogenous donor oligonucleotides, that is between about 12 to about 150 bp in length. In some cases, the double stranded exogenous donor oligonucleotide is between about 20 to about 75 bp in length. In some cases, the double stranded exogenous donor oligonucleotide is between about 30 to about 75 bp in length. In some cases, the double stranded exogenous donor oligonucleotide is between about 25 to about 50 bp in length. In some cases, the double stranded exogenous donor oligonucleotide is between about 25 to about 40 bp in length. In some cases, the double stranded exogenous donor oligonucleotide is, or is about, 34 bp in length. Any one of the foregoing exogenous donor oligonucleotides, analogs thereof, or combinations thereof, can be contacted with a cell or contacted with a genome in a cell under conditions suitable to insert the exogenous donor oligonucleotide, or fragment thereof, into double stranded break points in the genome of the cell and detected to quantitate double stranded break points in the genome of the cell.

Described herein is a partitioned (e.g., partitioned in an emulsion droplet or microwell) genomic nucleic acid fragment having an inserted exogenous donor oligonucleotide, or fragment thereof. Similarly, described herein is a mixture partition (e.g., mixture partition in or containing an emulsion droplet or in a microwell) containing a genomic nucleic acid fragment having an inserted exogenous donor oligonucleotide, or fragment thereof. Also described herein is a plurality of partitioned (e.g., partitioned in an emulsion droplet or microwell) genomic nucleic acid fragments, wherein at least one of the plurality contains an inserted exogenous donor oligonucleotide, or fragment thereof. Also described herein is a plurality of mixture partitions (e.g., mixture partitions that are in or contain emulsion droplets or are in a microwell) containing genomic nucleic acid fragments, wherein at least one of the genomic nucleic acid fragments has an inserted exogenous donor oligonucleotide, or fragment thereof. For example, the plurality of partitioned nucleic acid fragments or plurality of mixture partitions can be, can be about, can be at least, or can be at least about, 2; 3; 4; 5; 6; 8; 10; 15; 20; 25; 30; 35; 40; 45; 50, 60; 70; 80; 90; 100; 125; 150; 175; 200; 225; 250; 275; 300; 325; 350; 375; 400; 425; 450; 475; 500; 550; 600; 650; 700; 750; 800; 900; 1,000; 1,250; 1,500; 2,000; 3,000; 4,000; 5,000; 7,500; 9,000; 10,000; 12,000; 15,000; 20,000; 50,000; 75,000; 100,000; or more such partitioned nucleic acid fragments or mixture partitions containing such partitioned nucleic acid fragments.

III. Kits

Described herein are kits for performing any of the methods described herein, or combinations thereof, or for generating any of the compositions described herein, or combinations thereof. Such kits can include one or more of the following: an exogenous donor oligonucleotide, a probe that specifically detects amplification of a heterologous sequence generated by circularization of a genomic nucleic acid fragment of a cell, a probe that specifically detects amplification of an endogenous genomic sequence of a cell, a probe that specifically detects amplification of a sequence proximal to an (e.g., on-target) genome-editing reagent cleavage site fragmenting reagents (e.g., buffers, salts, and/or enzymes), reagents for partitioning genomic nucleic acid fragments (e.g., linear, circularized, or linearized fragments), circularization reagents (e.g., buffers, salts, and/or enzymes such as polymerase and/or ligase), linearization reagents (e.g., primers, buffers, salts, and/or enzymes), amplification reagents (e.g., primers, buffers, salts, and/or enzymes such as polymerase), an intercalating dye, or an exogenous control polynucleotide having a sequence that is not present in the genome of a cell. In some cases, the sequence of the control polynucleotide is not present in a circularized fragment of a genome of a cell. In some cases, the sequence of the control polynucleotide is not present in the exogenous donor oligonucleotide.

All patents, patent applications, and other publications, including GenBank Accession Numbers, cited in this application are incorporated by reference in the entirety for all purposes.

EXAMPLES

The following example is provided by way of illustration only and not by way of limitation. Those of skill in the art will readily recognize a variety of non-critical parameters that could be changed or modified to yield essentially the same or similar results.

Example 1

Cells are contacted with a genome editing reagent and an exogenous donor oligonucleotide under conditions suitable to generate targeted double strand break points and insertion of the exogenous donor oligonucleotide into one or more of the targeted double strand break points. Genomic nucleic acid is extracted, fragmented, and circularized. The circularized fragments are mixed with amplification reagents and partitions. The partitions are incubated under conditions suitable to generate amplicons in partitions containing a genomic fragment into which an exogenous donor oligonucleotide, or portion thereof, has been inserted. Partitions containing such amplicons are detected and quantitated. The number of partitions containing such amplicons indicates the number of double stranded break points in the genomes of the contacted cells.

What is claimed is:
1. A method for quantitating a number of double-stranded break points in a genome of a cell, the method comprising:
a) providing genomic nucleic acid from the cell, wherein the genomic nucleic acid has an exogenous donor polynucleotide, or a portion thereof, inserted into double-stranded break points in the cell;
b) fragmenting the genomic nucleic acid to generate a plurality of genomic nucleic acid fragments, wherein at least one of the genomic nucleic acid fragments contains the inserted donor polynucleotide or the portion thereof;
c) generating a plurality of mixture partitions containing circular genomic nucleic fragments and a pair of amplification primers, wherein the circular genomic nucleic acid fragments are generated by circularizing the genomic nucleic acid fragments either prior to or after the partitions are generated, wherein the pair of amplification primers are complementary to opposite strands of the donor polynucleotide or portion thereof, and wherein the pair of amplification primers are oriented such that the 5' ends are proximal to each other and the 3' ends are distal to each other when hybridized to a genomic nucleic fragment containing the inserted donor polynucleotide or portion thereof before circularization;
d) amplifying the genomic nucleic fragments with the pair of amplification primers to selectively generate amplicons in mixture partitions that contain one or more genomic fragments containing the inserted donor polynucleotide or portion thereof;

e) detecting the amplicons; and
f) counting the number of mixture partitions containing amplicons, thereby quantitating a number of double-stranded break points in the genome of the cell.

2. The method of claim 1, wherein the generating the plurality of mixture partitions containing circular genomic nucleic fragments comprises circularizing the genomic nucleic acid fragments and partitioning the circularized genomic nucleic fragments into a plurality of mixture partitions.

3. The method of claim 1, wherein the generating the plurality of mixture partitions containing circular genomic nucleic fragments comprises partitioning the genomic nucleic fragments into a plurality of mixture partitions and circularizing the genomic fragments in the partitions.

4. The method of claim 1, wherein the method further comprises performing steps a)-f) for a population of cells, thereby quantitating a number of double-stranded break points in the genomes of the population of cells.

5. The method of claim 1, wherein at least one of the double-stranded break points is induced by an exogenous genome editing reagent.

6. The method of claim 1, wherein the donor polynucleotide is a double-stranded donor polynucleotide.

7. The method of claim 6, wherein the double-stranded donor polynucleotide is from 20 to 150 bp in length.

8. The method of claim 1, wherein the 5' ends of the pair of amplification primers hybridize to an overlap region on opposite strands of the donor polynucleotide.

9. The method of claim 8, wherein the overlap region is from 1-10 nucleotides in length.

10. The method of claim 1, wherein the method comprises linearizing circular genomic nucleic fragments that contain the inserted donor polynucleotide or portion thereof in the partitions and amplifying the linearized circular genomic nucleic acid fragments.

11. The method of claim 10, wherein the linearizing comprises cleaving the inserted donor polynucleotide or portion thereof.

12. The method of claim 1, wherein the circularizing comprises ligation.

13. The method of claim 1, wherein the step of detecting the amplicons comprises detecting an increase in fluorescence of an intercalating dye in the presence of a double-stranded DNA amplicon.

14. The method of claim 13, wherein the increase in fluorescence of the intercalating dye in the mixture partitions is quantified to thereby detect a size of the amplicons in the mixture partitions.

15. The method of claim 1, wherein the method further comprises detecting a sequence proximal to an on-target genome-editing reagent cleavage site with a hydrolysis probe or a molecular beacon, wherein the sequence proximal to an on-target genome-editing reagent cleavage site comprises:
i) an endogenous nucleic acid sequence of the genome; or
ii) a heterologous sequence that is heterologous to the genome of the organism and is generated by ligation of two endogenous non-consecutive genomic nucleic acid fragments.

16. The method of claim 15, wherein the method comprises counting the number of mixture partitions that contain an amplicon and a sequence proximal to an on-target genome-editing reagent cleavage site, thereby detecting a number of on-target genome insertions.

17. The method of claim 16, wherein the method comprises comparing the ratio of i) to ii), wherein:
i) is a number of mixture partitions containing an amplicon and a sequence proximal to an on-target genome-editing reagent cleavage site; and
ii) is a number of mixture partitions containing an amplicon,
thereby determining a rate of on-target genome editing by a genome editing reagent or method.

18. The method of claim 15, wherein the method comprises counting the number of mixture partitions that contain an amplicon and do not contain a sequence proximal to an on-target genome-editing reagent cleavage site, thereby detecting a number of off-target genome insertions.

19. The method of claim 18, wherein the method comprises comparing the ratio of i) to ii), wherein:
i) is a number of mixture partitions that contain an amplicon and do not contain a sequence proximal to an on-target genome-editing reagent cleavage site; and
ii) is a number of mixture partitions containing an amplicon,
thereby determining a rate of off-target genome insertions by a genome editing reagent or method.

20. A method for detecting or quantifying a number of double-stranded break points in a genome of a cell comprising:
providing genomic nucleic acid fragments, wherein at least a portion of the genomic nucleic acid fragments comprise an inserted exogenous donor oligonucleotide;
partitioning the genomic nucleic acid fragments into a plurality of partitions, wherein each of the partitions further comprises a forward amplification primer and a reverse amplification primer that hybridize to the exogenous donor oligonucleotide sequence;
incubating the partitions under conditions suitable to selectively amplify genomic nucleic acid fragments that comprise an insertion, thereby forming selective amplification products;
detecting the selective amplification products in the partitions; and
quantifying the number of partitions in which a selective amplification product is detected.

21. The method of claim 1, wherein the generating step comprises generating a sufficient number of partitions such that substantially all of the partitions have no more than one genomic nucleic acid fragment.

* * * * *